(12) United States Patent
Rourke et al.

(10) Patent No.: US 8,778,398 B2
(45) Date of Patent: *Jul. 15, 2014

(54) IMMEDIATE RELEASE FORMULATIONS AND DOSAGE FORMS OF GAMMA-HYDROXYBUTYRATE

(75) Inventors: Andrea Marie Rourke, Belmont, CA (US); Maura Patricia Murphy, Baltimore, MD (US); James Frederick Pfeiffer, Oakland, CA (US); Clark Patrick Allphin, Los Altos, CA (US); Alya Khan McGinlay, Belmont, CA (US)

(73) Assignee: Jazz Pharmaceuticals, Inc., Palo Alto, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 12/773,599

(22) Filed: May 4, 2010

(65) Prior Publication Data

US 2011/0111027 A1    May 12, 2011

(51) Int. Cl.
    *A61K 9/36*    (2006.01)
(52) U.S. Cl.
    USPC .......................................................... 424/479
(58) Field of Classification Search
    USPC .................................................. 424/400, 479
    See application file for complete search history.

(56) References Cited

U.S. PATENT DOCUMENTS

| | | | |
|---|---|---|---|
| 3,051,619 | A | 8/1962 | Laborit |
| 4,374,441 | A | 2/1983 | Carter et al. |
| 4,393,236 | A | 7/1983 | Klosa |
| 4,738,985 | A | 4/1988 | Kluger et al. |
| 4,916,161 | A | 4/1990 | Patell |
| 4,983,632 | A | 1/1991 | Gessa et al. |
| 5,294,430 | A | 3/1994 | Borch et al. |
| 5,380,937 | A | 1/1995 | Koehler et al. |
| 5,594,030 | A | 1/1997 | Conte et al. |
| 5,753,708 | A | 5/1998 | Koehler et al. |
| 5,840,331 | A | 11/1998 | Van Cauter et al. |
| 5,990,162 | A | 11/1999 | Scharf |
| 6,384,020 | B1 | 5/2002 | Flanner et al. |
| 6,436,998 | B1 | 8/2002 | Cacciaglia et al. |
| 6,472,431 | B2 | 10/2002 | Cook et al. |
| 6,472,432 | B1 | 10/2002 | Perricone |
| 6,780,889 | B2 | 8/2004 | Cook et al. |
| 7,262,219 | B2 | 8/2007 | Cook et al. |
| 7,851,506 | B2 | 12/2010 | Cook et al. |
| 8,263,650 | B2 | 9/2012 | Cook et al. |
| 8,324,275 | B2 | 12/2012 | Cook et al. |
| 8,461,203 | B2 | 6/2013 | Cook et al. |
| 2004/0092455 | A1 | 5/2004 | Mamelak et al. |
| 2005/0031688 | A1 | 2/2005 | Ayala |
| 2005/0142192 | A1 | 6/2005 | Benjamin et al. |
| 2006/0018933 | A1 | 1/2006 | Vaya et al. |
| 2006/0024365 | A1 | 2/2006 | Vaya et al. |
| 2006/0210630 | A1 | 9/2006 | Liang et al. |
| 2007/0270491 | A1 | 11/2007 | Cook et al. |
| 2008/0069871 | A1 | 3/2008 | Vaughn et al. |
| 2008/0292700 | A1 | 11/2008 | Nghiem et al. |
| 2008/0293698 | A1 | 11/2008 | Johnson |
| 2010/0112056 | A1 | 5/2010 | Rourke et al. |
| 2011/0039929 | A1 | 2/2011 | Cook et al. |
| 2012/0020833 | A1 | 1/2012 | Cook et al. |
| 2012/0076865 | A1 | 3/2012 | Allphin et al. |
| 2012/0202879 | A1 | 8/2012 | Cook et al. |
| 2012/0202880 | A1 | 8/2012 | Cook et al. |

FOREIGN PATENT DOCUMENTS

| | | |
|---|---|---|
| EP | 0235408 | 9/1987 |
| EP | 0344704 | 12/1989 |
| EP | 0616804 | 9/1994 |
| EP | 0635265 | 1/1995 |
| EP | 1140061 | 10/2001 |
| GB | 0922029 | 3/1963 |
| JP | 57042651 | 3/1982 |
| JP | 04049212 | 2/1992 |
| JP | 05508422 | 11/1993 |
| RU | 2210360 | 8/2003 |
| WO | WO 96/40105 | 12/1996 |
| WO | WO 2006/053186 | 5/2006 |
| WO | WO 2010/053691 | 5/2010 |
| WO | WO2011/119839 | 9/2011 |
| WO | WO2011/139271 | 11/2011 |

OTHER PUBLICATIONS

Notification of Transmittal of the International Search Report and the Written Opinion of the International Searching Authority issued Dec. 18, 2009 in International Application No. PCT/US2009/061312.
Notification of Transmittal of the International Search Report and the Written Opinion of the International Searching Authority issued Jan. 18, 2011 in International Application No. PCT/US2010/033572.
Broughton, et al. "Gamma-Hydroxy-Butyrate in the Treatment of Narcolepsy: A Preliminary Report," (1976) Narcolepsy, Ny, N.Y., Spectrum Publications, Inc. (1976) 659-668.
Broughton, et al. "The Treatment of Narcolepsy-Cataplexy with Nocturnal Gamma-Hydroxybutyrate," (1979) Can J. Neurol Sci (1979) 6:1-6.
Broughton, et al. "Effects of Nocturnal Gamma-Hydroxybutyrate on Sleep/Waking Patterns in Narcolepsy-Cataplexy," (1980) Can J. Neurol Sci (1980) 7:23-30.
Frucht, et al. "A Pilot Tolerability and Efficacy Trial of Sodium Oxybate in Ethanol-Responsive Movement Disorders," (2005) Movement Disorders, 20(10):1330.
L. Borgen, et al. "Xyrem® (sodium oxybate): A Study of Dose Proportionality in Healthy Human Subjects," (2000) J, Clin. Pharmacol., 40:1053.

(Continued)

*Primary Examiner* — David J Blanchard
*Assistant Examiner* — Devang Thakor
(74) *Attorney, Agent, or Firm* — Seed IP Law Group PLLC

(57) ABSTRACT

The present invention provides a solid immediate release dosage form adapted for oral administration of GHB. The solid immediate release dosage form includes an immediate release formulation comprising a relatively high weight-percentage of GHB with a bioavailability similar to that of a liquid GHB dosage form.

19 Claims, 3 Drawing Sheets

(56) References Cited

OTHER PUBLICATIONS

Mamelak, et al. "The Effects of y-Hydroxybutyrate on Sleep," (1977) Biol Psych (1977) 12:273-288.
Remington. The Science and Practice of Pharmacy. 20th Edition, Gennaro, Ed,. Lippincott Williams & Wilkins (2000). (See e.g. p. 861).
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Preliminary Amendment filed Mar. 24, 2011 in co-pending U.S. Appl. No. 13/071,369.
Notification of Transmittal of the International Search Report and the Written Opinion of the International Searching Authority issued May 17, 2011 in International Application No. PCT/US2011/029802, now WO2011/119839.
Notification Concerning Transmittal of International Preliminary Report on Patentability issued May 19, 2011 in International Application No. PCT/US2009/061312, now WO2010/053691.
Extended European Search Report issued Mar. 23, 2012 in co-pending European Patent Application No. 09825191.1.
Office Action issued Jul. 6, 2011 in co-pending U.S. Appl. No. 12/264,709, now US2010/0112056.
Response to Jul. 6, 2011 Office Action filed on Oct. 6, 2011 in co-pending U.S. Appl. No. 12/264,709, now US 2010/0112056.
Final Office Action issued Dec. 29, 2011 in co-pending U.S. Appl. No. 12/264,709, now US 2010/0112056.
Response to Dec. 29, 2011 Final Office Action filed Feb. 29, 2012 in co-pending U.S. Appl. No. 12/264,709, now US 2010/0112056.
Advisory Action issued Mar. 12, 2012 in co-pending U.S. Appl. No. 12/264,709, now US 2010/0112056.
Response to the Mar. 12, 2012 Advisory Action filed Jun. 29, 2012 in co-pending U.S. Appl. No. 12/264,709, now US 2010/0112056.
Lubrano, et al. "Fibromyalgia in Patients with Irritable Bowel Syndrome. An Association with the Severity of the Intestinal Disorder." Int J Colorectal Dis. Aug. 2001;16(4):211-5.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med., 37, 341 (1975).
Outlaw, et al. "Dyspepsia and its Overlap with Irritable Bowel Syndrome." Curr Gastroenterol Rep. Aug. 2006;8(4):266-72.
Remington. The Science and Practice of Pharmacy. 20th Edition, Gennaro, Ed,. Lippincott Williams & Wilkins. Chapter 45 (Oral Solid Dosage Forms) (2000).
Notification Concerning Transmittal of International Preliminary Report on Patentability issued Nov. 15, 2012 in International Application No. PCT/US2010/033572.
First Office Action issued Feb. 27, 2013 in U.S. Appl. No. 13/071,369.
Response to First Office Action issued Feb. 27, 2013 in U.S. Appl. No. 13/071,369, filed May 28, 2013.
Notification Concerning Transmittal of the International Preliminary Report on Patentability issued Oct. 4, 2012 in International Application No. PCT/US2011/029802.
Arena, et al., "Absorption of Sodium Y-Hydroxybutyrate and Its Prodrug Y-Butyrolactone: Relationship Between In Vitro Transport and In Vivo Absorption," Journal of Pharmaceutical Sciences, 69(3), Mar. 1980, 356-358.
Bedard, "Nocturnal y-Hydroxybutyrate—Effect on Periodic Leg Movements and Sleep Organization of Narcoleptic Patients," Clin Neuropharmacol., 12(1), Feb. 1989, 29-36.
Berner, Jon E., "A Case of Sodium Oxybate Treatment of Tardive Dyskinesia and Bipolar Disorder," J. Clin. Psychiatry, 2008, 69:5, p. 862.
Berthier, et al., "Possible Involvement of a Gamma-Hydroxybutyric Acid Receptor in Startle Disease," Acta Paediatr, 83, 1994, 678-680.
Ferrara, S. D., et al., "Pharmacokinetics of Y-Hydroxybutyric Acid in Alcohol Dependent Patients After Single and Repeated Oral Doses," Br. J. Clin. Pharmacol., 34, (1992), 231-235.

Ferris, T.J., et al., "Synthesis, characterisation and detection of gamma-hydroxybutyrate salts," Forensic Science International, 2012, 216: 158-162.
Frucht, S.J., et al., "A Single-Blind, Open-Label Trial of Sodium Oxybate for Myoclonus and Essential Tremor," Neurology, 2005, 65: 1967-1970.
Gallimberti, L., "Gamma-Hydroxybutric Acid in the Treatment of Alcohol Dependence: A Double-Blind Study," Alcohol Clin. Exp. Res., 16(4), (1992), 673-676.
Gallimberti, L., "Gamma-hydroxybutyric Acid for Treatment of Alcohol Withdrawal Syndrome," Clinical Pharmacology, 2(8666), (1989), 787-789.
Gerra, G., et al., "Flumazenil effects on growth hormone response to gamma-hydroxybutyric acid," Int Clin Psychopharmacol., 9(3), (Sep. 1994), 211-5.
Gessa, G. L., et al., "Gamma-hydroxybutyric acid (GHB) for treatment of ethanol dependence," European Neuropsychopharmacology, 3(3), (1993), 224-225.
Gessa, G. L., "Gamma-hydroxybutyric Acid in the Treatment of Alcohol Dependence," Clin. Neuropharm., 15 Suppl 1 Pt A, (1992), 303a-304a.
Grove-White, I. G., "Critical Flicker Frequency after Small Doses of Methohexitone, Diazepam and Sodium 4-Hydroxybutyrate," Brit. J. Anaesth, 43(2), (1971), 110-2.
Grove-White, I. G., et al., "Effect of Methohexitone, Diazepam and Sodium 4-Hydroxybutyrate on Short-Term Memory," Brit. J. Anaesth, 43(2), (1971), 113-116.
Hasenbos, M. A., et al., "Anaesthesia for bullectomy. A technique with spontaneous ventilation and extradural blockade," Anaesthesia, 40(10), (1985), 977-980.
Hoes, M. J., "Gamma-hydroxybutyric acid (*) as hypnotic. Clinical and pharmacokinetic evaluation of gamma-hydroxybutyric acid as hypnotic in man," L Encephale, vol. 1, (1980), 93-99.
Laborit, H., "Gamma-Hydroxybutyrate, Succinic Semialdehyde and Sleep," Laboratoire d'Eutonologie, (1973), 257-274.
Ladinsky, et al., "Mediation by the Corticostriatal Input of the In Vivo increase in Rat Striatal Acetylcholine content induced by 2-Chloroadenosine," Biochemical Pharm. vol. 32, No. 19, pp. 2993-2996 (1983).
Ladinsky, H., et al., "Mode of Action of Gamma-Butyrolactone on the Central Cholinergic System, Naunyn-Schmiedeberg's," Arch. Pharmacol., 322, (1983), 42-48.
Lammers, G. J., "Gammahydroxybutyrate and Narcolepsy: A Double-Blind Placebo-Controlled Study," Sleep, 16(3), (1993), 216-220.
Lapierre, O., "The Effect of Gamma-Hydroxybutyrate on Nocturnal and Diurnal Sleep of Normal Subjects: Further Considerations on REM Sleep-Triggering Mechanisms," Sleep, 13, (1990), 24-30.
Lee, C. R., "Evidence for the β-Oxidation of Orally Administered 4-Hydroxybutyrate in Humans," Biochemical Medicine, 17(3), (1977), 284-291.
Lettieri, J., et al., "Improved Pharmacological Activity via Pro-Drug Modification: Comparative Pharmacokinetics of Sodium Y-Hydroxybutyrate and Y-Butyrolactone," Research Communications in Chemical Pathology and Pharmacology, 22(1), (1978), 107-118.
Mamelak, M., "Gammahydroxybutyrate: An Endogenous Regulator of Energy Metabolism," Neuroscience and Biobehavioral Reviews, 13(4), (1989), 187-198.
Mamelak, M., "Sleep-Inducing Effects of Gammahydroxybutyrate," The Lancet, 2(7824), (1973), 328-3.
Mamelak, M., et al., "Treatment of Narcolepsy and Sleep Apnea with Gammahydroxybutyrate: A clinical and polysomnographic case study," Sleep, 4(1), (1981), 105-11.
Mamelak, M., et al., "Treatment of Narcolepsy with y-hydroxybutyrate. A review of Clinical and Sleep Laboratory Findings," Sleep, 9(1), (1986), 285-90.
Morrison, Robert Thornton, et al., Organic Chemistry, 3rd Edition, (1973), pp. 672-677.
Nema, S, et al., "Excipients and Their Use in Injectable Products," PDA J. Pharm. Sci. Technol, 51(4), (1997), 166-171.
Neuman, Ariel, "GHB's Path to Legitimacy: An Administrative and Legislative History of Xyrem," (2004), 1-39.

(56) References Cited

OTHER PUBLICATIONS

Ondo, William G., et al., "Sodium Oxybate for Excessive Daytime Sleepiness in Parkinson's Disease: A Polysomnographic Study," Arch. Neural. 2008, 65(10).
Palatini, P., "Dose Dependent Absorption and Elimination of Gamma-Hydroxybutyric Acid in Healthy Volunteers," Eur. J. Clin. Pharmacol., 45(4), (1993), 353-356.
Roth, et al., "y-Butyrolactone and y-Hydroxybutyric Acid-I, Distribution and Metabolism," Biochemical Pharmacology, 15, (1966), 1333-1348.
Roth, R. H., et al., "y-Butyrolactone and y-Hydroxybutyric acid-II. The Pharmacologically active form," J. Neuropharmacol. 5, (1966), 421-428.
Russel, I. Jon, et al., "Sodium Oxybate Relieves Pain and Improves Function in Fibromyalgia Syndrome," Arthritis. Rheum., 2009, 60: 299-309.
Scharf, Martin B., et al., "The Effects of Sodium Oxybate on Clinical Symptoms and Sleep Patterns in Patients with Fibromyalgia," J. Rheumatol, 2003, 30(5): 1070-1074.
Scharf, M. B., "The Effects and Effectiveness of y-Hydroxybutyrate in Patients with Narcolepsy," J. Clin. Psychiatry, 46(6), (1985), 222-225.
Scharf, M. B., et al., "GHB—New Hope for Narcoleptics?," Biol Psychiatry, 26(4), (Aug. 1989), 329-30.
Scrima, et al., "Effect of Gamma-Hydroxybutyrate on a Patient with Obstructive Sleep Apnea," Sleep Research, 16, (1987), 137.
Scrima, et al., "Effect of High Altitude on a Patient with Obstructive Sleep Apnea," Sleep Research, 16, (1987), 427.
Scrima, et al., "Effects of Gamma-Hydroxybutyrate (GHB) on Narcolepsy-Cataplexy Symptoms and MSLT Results in Male and Female Patients," Association of Professional Sleep Societies, (1988), 251.
Scrima, et al., "Gamma-Hydroxybutyrate Effects on Cataplexy and Sleep Attacks in Narcoleptics," Sleep Research, 16, (1987), 134.
Scrima, L., et al., "Efficacy of Gamma-Hydroxybutyrate Versus Placebo in Treating Narcolepsy-Cataplexy: Cataplexy: Double-Blind Subjective Measures," Biol. Psychiatry, 26(4), (1989), 331-343.
Scrima, L., "The Effects of Y-Hydroxybutyrate on the Sleep of Narcolepsy Patients: A Double-Blind Study," Sleep, 13(6), (1990), 479-490.
Scrima, L., et al., "Narcolepsy," New England J. Med., 324(4), (1991), 270-272.
Series, F., "Effects of Enhancing Slow-Wave Sleep by Gamma-Hydroxybutyrate on Obstructive Sleep Apnea," Am. Rev. Respir. Dis., 145(6), (1992), 1378-1383.
Snead, et al., "Ontogeny of y-Hydroxybutyric Acid. I. Regional Concentration in Developing Rat, Monkey and Human Brain," Brain Res., 227(4), (1981), 579-589.
Snead, O. Carter, "y-Hydroxybutyrate Model of Generalized Absence Seizures: Further Characterization and Comparison with Other Absence Models," Epilepsia, 1988, 29(4): 361-368.
Stock, G., "Increase in brain dopamine after axotomy or treatment with Gammahydroxybutyric acid due to elimination of the nerve impulse flow," Naunyn-Schmiedeberg's Arch. Pharmacol., 278(4), (1973), 347-361.
Strong, A.J., "y-Hydroxybutyric acid and intracranial pressure," The Lancet, (1984), 1304.
Suner, Selim, et al., "Pediatric Gamma Hydroxybutyrate Intoxication," Acad Emerg. Med., vol. 4, (1997), 1041-1045.
Tunnicliff, Godfrey, "Sites of Action of Gamma-Hydroxybutyrate (GHB)—A Neuroactive Drug with Abuse Potential," Clinical Toxicology, 35(6), 581-590 (1997).
Van Den Bogert, A. G., et al., "Placentatransfer of 4-hydroxybutyric acid in man," Anaesthesiology and Intensive Care Medicine, 110, (1978), 55-64.
Vickers, M.D., "Gammahydroxybutyric Acid," Int. Anesth. Clinic, 7(1), (1969), 75-89.
Yamada, Y., "Effect of Butyrolactone and Gamma-Hydroxybutyrate on the EEG and Sleep Cycle in Man," Electroenceph. clin. Neurophysiol., 22, (1967), 558-562.

21 C.F.R. 184, Food and Drug Administration, HHS, (1998), pp. 441-535.
Activase, Physicians Desk Reference (50th ed.), (1996), pp. 312, 1058-1061.
Chem Abstract ES302338, SciFinder®, (1964), 1 pg.
Chemical Abstracts: Seventh Collective Index, vols. 56-65, (1962-1966), 4 pgs.
"HIB-IMUNE," Physicians Desk Reference (41st ed.), (1987), 1095-1096.
"HibVAX," Physicians Desk Reference (41st ed.), (1987), 870.
"Malic Acid," The Handbook of Pharmaceutical Excipients, 2nd Ed., (1994), pp. 285-286, 633.
Phospholine Iodide, Physicians Desk Reference (50th ed.), (1996), 2784.
"Taxotere," Physicians Desk Reference (51st ed.), (1997), 2204-2207.
United States Pharmacopeial Convention, Inc.: The National Formulary, 23/NF18, (1995), p. 2205.
Restriction Requirement issued Mar. 19, 2001 in U.S. Appl. No. 09/470,570.
Response to Restriction Requirement filed May 3, 2001 in U.S. Appl. No. 09/470,570.
Response to Office Action filed Aug. 10, 2001 in U.S. Appl. No. 09/470,570.
Office Action issued Oct. 25, 2001 in U.S. Appl. No. 09/470,570.
Preliminary Amendment filed Nov. 29, 2001 in U.S. Appl. No. 09/470,570.
Office Action issued Dec. 13, 2001 in U.S. Appl. No. 09/470,570.
Response to Office Action filed Mar. 6, 2002 in U.S. Appl. No. 09/470,570.
Notice of Allowance issued Apr. 18, 2002 in U.S. Appl. No. 09/470,570.
Supplementary Notice of Allowance issued Sep. 17, 2002 in U.S. Appl. No. 09/470,570.
Office action issued May 25, 2001 in U.S. Appl. No. 09/470,570.
Notice of allowance issued Mar. 24, 2004 in U.S. Appl. No. 10/194,021.
Preliminary Amendment filed Jul. 11, 2002 in U.S. Appl. No. 10/194,021.
Preliminary Amendment filed May 8, 2004 in U.S. Appl. No. 10/841,709.
Office Action issued Nov. 30, 2006 in U.S. Appl. No. 10/841,709.
Response filed Feb. 21, 2007 to Office Action issued Nov. 30, 2006 in U.S. Appl. No. 10/841,709.
Examiner Interview Summary issued Apr. 27, 2007 in U.S. Appl. No. 10/841,709.
Notice of Allowance issued May 25, 2007 in U.S. Appl. No. 10/841,709.
Restriction Requirement issued Jul. 14, 2008 in U.S. Appl. No. 11/777,877.
Response filed Jul. 31, 2008 to Restriction Requirement issued Jul. 14, 2008 in U.S. Appl. No. 11/777,877.
Office Action issued Nov. 6, 2008 in U.S. Appl. No. 11/777,877.
Response filed Apr. 2, 2009 to Office Action issued Nov. 6, 2008 in U.S. Appl. No. 11/777,877.
Final Office Action issued Jul. 10, 2009 in U.S. Appl. No. 11/777,877.
Response filed Jan. 11, 2010 to Final Office Action issued Jul. 10, 2009 in U.S. Appl. No. 11/777,877.
Office Action issued Feb. 3, 2010 in U.S. Appl. No. 11/777,877.
Response filed Jul. 28, 2010 to Office Action issued Feb. 3, 2010 in U.S. Appl. No. 11/777,877.
Notice of Allowance issued Oct. 8, 2010 in U.S. Appl. No. 11/777,877.
Preliminary Amendment filed Jan. 10, 2011 in U.S. Appl. No. 12/913,644.
Office Action issued May 25, 2012 in U.S. Appl. No. 12/913,644.
Supplemental Preliminary Amendment filed Apr. 13, 2012 in U.S. Appl. No. 13/182,324.
Office action issued Jul. 16, 2012 in U.S. Appl. No. 13/182,324.
Response filed Jan. 16, 2013 to Office Action issued Jul. 16, 2012 in U.S. Appl. No. 13/182,324.

(56) References Cited

OTHER PUBLICATIONS

Notice of Allowance issued Jan. 30, 2013 in U.S. Appl. No. 13/182,324.
Office Action issued Jun. 28, 2012 in U.S. Appl. No. 13/446,892.
Response filed Aug. 24, 2012 to Office Action issued Jun. 28, 2012 in U.S. Appl. No. 13/446,892.
Notice of Allowance issued Oct. 3, 2012 in U.S. Appl. No. 13/446,892.
Office Action issued Jun. 11, 2012 in U.S. Appl. No. 13/446,940.
Response filed Jul. 2, 2012 to Office Action issued Jun. 11, 2012 in U.S. Appl. No. 13/446,940.
Notice of Allowance issued Jul. 16, 2012 in U.S. Appl. No. 13/446,940.
Amendment filed Jul. 17, 2012 in U.S. Appl. No. 13/446,940.
Examiner Interview Summary issued Aug. 16, 2012 in U.S. Appl. No. 13/446,940.
Preliminary Amendment filed Feb. 19, 2013 in U.S. Appl. No. 13/685,561.
Supplemental Preliminary Amendment filed Mar. 5, 2013 in U.S. Appl. No. 13/685,561.
Examiner's Report issued Oct. 24, 2003 in Australian Application No. 20590/00.
Search Report issued Jan. 22, 2004 in Australian Application No. 20590/00.
Examiner's Report issued May 4, 2004 in Australian Application No. 20590/00.
Response filed Nov. 19, 2004 to Examiner's Report issued May 4, 2004 in Australian Application No. 20590/00.
Office Action issued Jun. 30, 2004 in Canadian Application No. 2,355,293.
Response filed Oct. 19, 2004 to Office Action issued Jun. 30, 2004 in Canadian Application No. 2,355,293.
Notice of Allowance issued Dec. 3, 2004 in Canadian Application No. 2,355,293.
European Search Report issued Apr. 11, 2003 in European Application No. 03075658.9.
Office Action issued Nov. 21, 2001 in European Application No. 99964320.8.
Response filed Feb. 27, 2002 to Office Action issued Nov. 21, 2001 in European Application No. 99964320.8.
Decision to Grant issued Mar. 20, 2003 in European Application No. 99964320.8.
Office Action issued Nov. 19, 2012 in Indian Application No. 2633/KOLNP/2007.
Examination Report issued Jul. 20, 2006 in Indian Application No. IN/PCT/2001/00688.
Response filed Jul. 9, 2007 to Examination Report issued Jul. 20, 2006 in Indian Application No. IN/PCT/2001/00688.
International Search Report issued Jul. 21, 2000 in International Application No. PCT/US99/30740.
Written Opinion issued Oct. 18, 2000 in International Application No. PCT/US99/30740.
Response filed Feb. 16, 2001 to Written Opinion issued Oct. 18, 2000 in International Application No. PCT/US99/30740.
International Preliminary Examination Report issued Mar. 26, 2001 in International Application No. PCT/US99/30740.
Notice of Allowance issued Jul. 2, 2006 in Israeli Application No. 143733.
Office Action issued Oct. 5, 2006 in Japanese Application No. 2000-590626.
Response filed Apr. 10, 2007 to Office Action issued Oct. 10, 2006 in Japanese Application No. 2000-590626.
Response filed Jan. 13, 2009 to Final Office Action issued Oct. 14, 2008 in Japanese Application No. 2000-590626.
Notice of Allowance issued Jun. 16, 2009 in Japanese Application No. 2000-590626.
Office Action issued Jan. 17, 2012 Japanese Application No. 2009-028694.
Response filed Jun. 19, 2012 to Office Action issued Jan. 17, 2012 in Japanese Application No. 2009-028694.
Office Action issued Jul. 31, 2012 in Japanese Application No. 2009-028694.
Response filed Jan. 17, 2013 to Office Action issued Jul. 31, 2012 in Japanese Application No. 2009-028694.
Notice of Allowance issued Feb. 5, 2013 in Japanese Application No. 2009-028694.
*Jazz Pharmaceuticals, Inc.* v *Roxane Laboratories, Inc.*, Civil Action No. 12-6761 (ES)(SCM) Identity of Prior Art Pursuant to Local Patent Rule 3.3(a), (2013).
Markman Opinion, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES), (Sep. 14, 2012).
Roxane Laboratories, Inc.'s Answer and Affirmative Defenses to Plaintiff's Complaint, (Jan. 4, 2013).
Roxane Laboratories, Inc.'s Answer, Affirmative Defenses and Counterclaims to Plaintiff's Complaint, (Dec. 29, 2010).
Roxane Laboratories, Inc.'s Answer, Affirmative Defenses and Counterclaims to Plaintiff's Complaint, (Mar. 9, 2011).
Roxane Laboratories, Inc.'s Answer, Affirmative Defenses and Counterclaims to Plaintiff's Complaint, (Jun. 1, 2011).
Roxane Laboratories, Inc.'s Answer, Affirmative Defenses and Counterclaims to Plaintiff's Complaint, (Nov. 9, 2012).
Roxane Laboratories, Inc.'s Intitial Invalidity and Noninfringement Contentions Pursuant to Local Patent Rule 3.6, (Apr. 14, 2011).
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).

IMMEDIATE RELEASE FORMULATIONS AND DOSAGE FORMS OF GAMMA-HYDROXYBUTYRATE

CROSS-REFERENCE TO RELATED APPLICATIONS

This application is a continuation-in-part of prior U.S. patent application Ser. No. 12/264,709, filed Nov. 4, 2008, the entire contents of which are hereby incorporated by reference herein.

BACKGROUND OF THE INVENTION

Initial interest in the use of sodium oxybate as a potential treatment for narcolepsy arose from observations made during the use of sodium oxybate (the sodium salt of gamma-hydroxybutyrate) for anesthesia. Unlike traditional hypnotics, sodium oxybate induces sleep that closely resembles normal, physiologic sleep (Mamelak et al., Biol Psych 1977: 12:273-288). Therefore, early investigators administered gamma-hydroxybturate (GHB) to patients suffering from disorders of disturbed sleep, including narcolepsy (Broughton et al. in Narcolepsy, NY, N.Y.: Spectrum Publications, Inc. 1976:659-668), where it was found to increase total nocturnal sleep time, decrease nocturnal awakenings and increase Stage 3-4 (slow wave) sleep. Three open-label and two placebo-controlled studies provided a body of evidence demonstrating that improvements in nocturnal sleep were associated with a reduction in cataplexy and improvements in excessive daytime sleepiness (Broughton et al., Can J. Neurol Sci 1979; 6:1-6, and Broughton et al., Can J. Neurol Sci 1980; 7:23-30)

Scharf et al. conducted an open-label study to evaluate the effects of GHB on the sleep patterns and symptoms of non-narcoleptic patients with fibromyalgia (Scharf et al., J Rheumatol 1998; 25: 1986-1990). Eleven patients with previously confirmed diagnosis of fibromyalgia who reported at least a 3-month history of widespread musculoskeletal pain in all body quadrants and tenderness in at least five specific trigger point sites participated in the study. Results showed that patients reported significant improvements in the subjective assessments of their levels of pain and fatigue over all 4 weeks of GHB treatment as compared to baseline, as well as a significant improvement in their estimates of overall wellness before and after GHB treatment.

WO 2006/053186 to Frucht describes an open label study of five patients with hyperkinetic movement disorders including ethanol responsive myoclonus and essential tremor. Sodium oxybate was reported to produce dose-dependent improvements in blinded ratings of ethanol responsive myoclonus and tremor and was said to be tolerated at doses that provided clinical benefit.

Xyrem® sodium oxybate oral solution, the FDA approved treatment for cataplexy and excessive daytime sleepiness associated with narcolepsy, contains 500 mg sodium oxybate/ml water, adjusted to pH=7.5 with malic acid. In man, the plasma half-life of sodium oxybate given orally is about 45 minutes and doses of 2.25 grams to 4.5 grams induce about 2 to 3 hours of sleep (See, L. Borgen et al., *J. Clin. Pharmacol.*, 40, 1053 (2000)). For optimal clinical effectiveness in narcolepsy, sodium oxybate must be given twice during the night, and is administered as an aqueous solution. For each dose, a measured amount of the oral solution must be removed from the primary container and transferred to a separate container where it is diluted with water before administration. The second dose is prepared at bedtime and stored for administration in the middle of the night. This regimen is cumbersome and may be susceptible to errors in the preparation of the individual doses. For this reason, a more convenient unit dosage form of the drug would be clinically advantageous. Sodium oxybate is highly water-soluble, hygroscopic and strongly alkaline. Paradoxically, despite its high water solubility, it can exhibit poor dissolution when formulated in a tablet with common excipients. These properties, along with the large amount of the drug that is required to achieve the clinical effect, present challenges in preparing solid unit dosage forms that are designed for immediate release of the sodium oxybate into the gastrointestinal tract of the user.

BRIEF DESCRIPTIONS OF THE DRAWINGS

Figure 3:
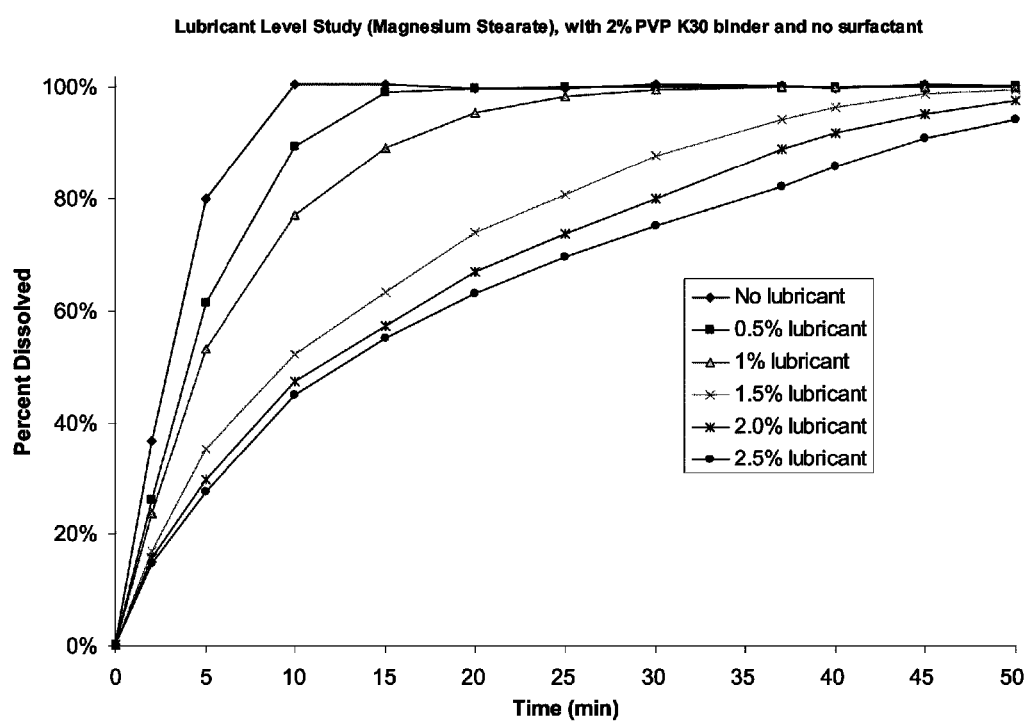

FIG. 3 graph showing the effect of lubricant on the dissolution profiles of immediate release formulations as disclosed herein.

DETAILED DESCRIPTION

Formulations and dosage forms for the immediate release of a drug are described herein. Formulations described herein are suited to the immediate release of high dose drugs that are highly water soluble. In addition, in certain embodiments, the formulations described herein provide immediate release of drugs that are highly hygroscopic, even where such drugs must be administered at relatively high doses. In particular embodiments, the immediate release formulations are provided as a unit dosage form, and certain embodiments, the immediate release formulation is provided as an immediate release tablet.

An example of a drug that may be used with the immediate release formulations and dosage forms described herein is GHB. It should be noted that embodiments of immediate release dosage forms comprising GHB are presented herein for purposes of example only and not for purposes of limitation. The formulations and unit dosage forms provided herein can be utilized to achieve immediate release of GHB, as well as pharmaceutically acceptable salts, hydrates, isomers, including tautomers, solvates and complexes of GHB. Suitable salts of GHB include sodium oxybate, calcium oxybate, as well as the lithium, potassium, and magnesium salts.

Administration of GHB in solid form presents several challenges. The amount of drug taken by the patient for each dose is high, generally at least 1.5 grams and as high as 4.5 grams. Patients treated with GHB may have difficulty taking solid medications by mouth either because they have disease states that make handling and swallowing difficult or because they must take the medication upon being awakened in the middle of the night. The situation is exacerbated by the large quantity of drug that is administered in each dose. Accordingly, it is desirable to keep the size of the tablet as small as possible while incorporating the largest amount of active ingredient. In addition, if an immediate release tablet is to achieve bioequivalency with the existing Xyrem® oral solution, such a formulation should dissolve quickly without high levels of excipients to speed dissolution.

As used herein, the term "GHB" refers to gamma-hydroxybutyrate, as well as pharmaceutically acceptable salts, hydrates, isomers, including tautomers, solvates and complexes of gamma-hydroxybutyrate. In certain embodiments, the immediate release GHB compositions described herein comprise a therapeutically effective amount of sodium oxybate or an alternative salt thereof. The structure of sodium oxybate is given below as formula (Ia):

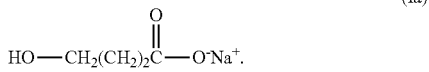

Alternative salts useful in an immediate release dosage form as disclosed herein include compounds of formula (I):

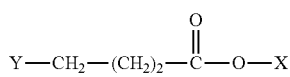

wherein X is a pharmaceutically-acceptable cation and may be selected from the group consisting of potassium, calcium, lithium and magnesium, and Y is OH. Sodium gamma-hydroxybutyrate (sodium oxybate), is currently available from Jazz Pharmaceuticals, Inc. as Xyrem® oral solution.

A "delivery rate" refers to the quantity of drug released in vivo from a formulation (tablet or dosage form) as disclosed herein per unit time, e.g., milligrams of a pharmaceutically acceptable salt, hydrate, isomer, tautomer, solvate or complex of GHB per unit time.

"Immediate release" refers to a composition that releases GHB or a pharmaceutically acceptable salt, hydrate, isomer, tautomer, solvate or complex of GHB substantially completely into the gastrointestinal tract of the user within a period of less than an hour, usually between about 0.1 and about 1 hour and less than about 0.75 hours from ingestion. Such a delivery rate allows the drug to be absorbed by the gastrointestinal tract in a manner that is bioequivalent to an oral solution. Where sodium oxybate is used as the drug and bioequivalence to the existing Xyrem® sodium oxybate oral solution is sought, rapid release of drug from the immediate release formulations described herein is desirable because following delivery of the Xyrem® oral solution, peak plasma concentration of sodium oxybate occurs within an hour. Such rapid absorption will typically occur for an immediate release unit dosage form, such as a tablet, caplet or capsule, if the drug included in such dosage form dissolves in the upper portion the gastrointestinal tract.

A "dissolution rate" refers to the quantity of drug released in vitro from a dosage form per unit time into a release medium. In vitro dissolution rates in the studies described herein were performed on dosage forms placed in a USP Type II bath containing water which is stirred while maintained at a constant temperature of 37° C. In some examples, aliquots of the dissolution media were injected into a chromatographic system to quantify the amounts of drug dissolved during each testing interval. In other cases, the dissolution was monitored with conductivity measurements using a dip probe.

By "bioavailability" as used herein is intended the estimated area under the curve, or AUC of the active drug in systemic circulation after oral administration with a dosage form as disclosed herein when compared with the AUC of the active drug in systemic circulation after oral administration of Xyrem® sodium oxybate oral solution. The AUC is affected by the extent to which the drug is absorbed in the GI tract. In the case of sodium oxybate, absorption tends to be greatest in the upper GI tract, so in particular embodiments, the immediate release formulations and dosage forms described herein include formulations that dissolve quickly in order to be bioequivalent to the Xyrem® oral solution.

Products are considered to be "bioequivalent" if the relative mean $C_{max}$, $AUC_{(0-t)}$ and $AUC_{(0-\infty)}$ of the test product to reference product is within 80% to 125%.

"Sodium oxybate oral solution" refers to the product currently known as Xyrem®, a solution that contains 500 mg sodium oxybate/ml water, adjusted to pH=7.5 with malic acid.

The term "$AUC_{0-t}$" means the area under the plasma concentration curve from time 0 to time t.

The term "$AUC_{0-\infty}$" or "$AUC_{0-inf}$" means the area under the plasma concentration time curve from time 0 to infinity.

"$C_{max}$" refers to the maximum plasma concentration of sodium oxybate. The $C_{max}$ of a 3 gram dose of immediate release tablets is between 10 and 200 µg/mL, often between 20 and 120 µg/mL. Such profiles are especially desirable for diseases such as narcolepsy, cataplexy, movement disorders such as essential tremor and restless leg syndrome, fibromyalgia and chronic fatigue syndrome.

"$T_{max}$" refers to the time to maximum plasma concentration for a given drug, which for sodium oxybate is between 0.5 and 2.5 hours, often between 0.5 and 1.5 hours/"$t_{1/2}$" refers to the time to reduce the plasma concentration by 50% during the terminal elimination phase of the drug, which for sodium oxybate is between 0.4 and 0.9 hours, often between 0.5 and 0.7 hours.

The apparent elimination rate constant is "$\lambda_z$", which for sodium oxybate may be between 0.5 and 2.5 hours$^{-1}$.

"Oxybate salt" refers to a compound of formula I wherein X is a pharmaceutically-acceptable cation and may be selected from the group consisting of sodium, potassium, calcium, lithium and magnesium and Y is OH.

"Sodium oxybate" refers to a compound of formula Ia.

Immediate release formulations suitable for oral administration may comprise unit dosage forms, such as tablets, caplets or filled capsules, which can deliver a therapeutically effective dose of GHB upon ingestion thereof by the patient of one or more of said dosage forms, each of which can provide a dosage of, for example, about 0.5-1.5 g of GHB. Additionally, the immediate release dosage forms can be shaped or scored to facilitate swallowing.

The formulation and structure of an immediate release dosage form as disclosed herein can be adjusted to provide immediate release performance that suits a particular dosing need. In particular, the formulation and structure of the dosage forms as described herein can be adjusted to provide any combination of the immediate release performance characteristics described herein. In particular embodiments, for example, an immediate release dosage form as disclosed herein provides rapid onset of action, releasing more than about 90%, such as, for example, more than about 95%, of the drug contained therein within a period of time selected from less than one hour, less than 45 minutes, less than 30 minutes and less than 15 minutes after administration.

Moreover, the rate of drug release from an immediate release dosage form as disclosed herein may be adjusted as needed to facilitate a desired dosing regimen or achieve targeted dosing. In one embodiment, the immediate release dosage form may be formulated to deliver as much as 2,000 mg of GHB. In particular embodiments, the total amount of drug contained within an immediate release dosage form according to the present description may be between about 500 mg and about 1,400 mg. For example, in certain such embodiments, the total amount of drug may be selected from between about 500 mg and 1,400 mg, 500 mg and 1,200 mg, 500 mg and 1,100 mg, 600 mg and 1,200 mg, 600 mg and 1,100 mg, 600 mg and 1,000 mg, 600 mg and 950 mg, 600 mg and 850 mg, 600 mg and 750 mg, 750 mg and 1,200 mg, 750 mg and 1,100 mg, 750 mg and 1,000 mg, 750 mg and 950 mg, and 750 mg and 850 mg.

Immediate release dosage forms described herein include immediate release formulations that facilitate high loading of GHB. For example, in particular embodiments, the immediate release formulations described herein may include between about 70% and 98% by weight GHB. In certain embodiments, an immediate release formulation as disclosed herein may comprise GHB in an amount selected from about 75%, 80%, 81%, 82%, 83%, 84%, 85%, 86%, 87%, 88%, 89%, 90%, 91%, 92%, 93%, 94%, 95%, 96%, 97%, and 98% by weight of the immediate release formulation. In certain such embodiments, the amount of GHB in the immediate release formulation may range from about 80-84%, 82-85%, 82-86%, 84-88%, 85-90%, 88-92%, 90-94%, 94-98%, 94-97%, 94-96%, 95-98%, 95-97%, and 95-96.5% by weight of the immediate release formulation. In particular embodiments, even with the high drug loading described herein, the immediate release formulations disclosed herein facilitate production of solid unit dosage forms that are bioequivalent to the Xyrem® sodium oxybate oral solution. In certain such embodiments, the solid unit dosage forms described herein release more than about 95% of the GHB contained therein within a period of less than one hour after administration.

The immediate release formulations provided herein generally include GHB and some level of lubricant to facilitate processing of the formulations into a unit dosage form. In some embodiments, therefore, the formulations described herein include a combination of GHB and lubricant, as described herein, and in certain such embodiments, the immediate release formulations are substantially free of other excipients or adjuvants. In other embodiments, the immediate release formulations described herein include a combination of GHB, lubricant, and binder, as described herein, and in certain such embodiments, the immediate release formulations are substantially free of other excipients or adjuvants. In yet other embodiments, the immediate release formulations described herein include a combination of GHB, lubricant, and surfactant, as described herein, and in certain such embodiments, the immediate release formulations are substantially free of other excipients or adjuvants. In still further embodiments, the formulations described herein include a combination of GHB, lubricant, binder, and surfactant, as described herein, and in certain such embodiments, the immediate release formulations are substantially free of other excipients or adjuvants. Though the immediate release formulations described herein may be formulated using a combination of drug and one or more of a lubricant, binder and surfactant, in certain embodiments, the compositions described herein may include one or more additional excipients selected from, for example, fillers, compression aids, diluents, disintegrants, colorants, buffering agents, coatings, glidants, or other suitable excipients.

To facilitate processing of the immediate release formulations described herein into unit dosage forms, the immediate release formulations will typically include some level of lubricant. For example, in particular embodiments, the immediate release formulation may include one or more lubricants selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, zinc stearate, and combinations of any of the foregoing. In certain embodiments, the one or more lubricants may be added to the immediate release formulation in an amount resulting in a total lubricant content of between about 0.5% and about 10% by weight. For example, in such embodiments, an immediate release formulation as disclosed herein may exhibit a total lubricant content in a range selected from about 0.5% to 5% by weight, about 1% to 5% by weight, about 4 to 10% by weight, about 4 to 8% by weight, about 6 to 10% by weight, about 1% to 3% by weight, about 1% to 2% by weight, about 2% to 3% by weight, and about 2% to 4% by weight. In one such embodiment, one or more lubricants may be present in the immediate release formulation, and the total lubricant content may be selected from about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% and 10% by weight. Where the immediate release formulation is provided as a tableted dosage form, still lower lubricant levels may be achieved with use of a "puffer" system during tableting. Such systems are known in the art, commercially available and apply lubricant directly to the punch and die surfaces rather than throughout the formulation.

In particular embodiments, the immediate release compositions described herein may include a lubricant selected from stearic acid and sodium stearyl fumarate, wherein the lubricant is included in the formulation in an amount of between about 0.5% and about 2% by weight. In another embodiment, an immediate release formulation as disclosed herein may comprise between about 0.5% and about 2%, by weight, magnesium stearate as a lubricant. In one such embodiment, magnesium stearate may be used in combination with one or more other lubricants or a surfactant, such as sodium lauryl sulfate. In particular, if needed to overcome potential hydrophobic properties of magnesium stearate, sodium lauryl sulfate may also be included when using magnesium stearate (Remington: the Science and Practice of Pharmacy, $20^{th}$ edition, Gennaro, Ed., Lippincott Williams & Wilkins (2000)).

In specific embodiments where the immediate release formulation comprises GHB in combination with a lubricant, the immediate release formulation may comprise from about 90-99% by weight GHB and about 1-10% by weight of a lubricant selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate. In one such embodiment, the immediate release formulation may comprise between about 98-99% by weight GHB and between about 1-2% by weight of the lubricant magnesium stearate. In another example, the immediate release formulation may comprise about 98-99% by weight GHB and about 1-2% by weight of a lubricant selected from stearic acid and sodium stearyl fumarate. In particular embodiments of the immediate release formulations incorporating a lubricant described herein, the GHB included in such formulations may be selected from sodium oxybate and calcium oxybate.

The immediate release formulations described herein can include one or more binders. Binders suitable for use in the immediate release formulations of the present description include, for example, hydroxypropyl cellulose (HPC), ethylcellulose, hydroxypropyl methylcellulose (HPMC), polyvinyl alcohol, polyvinyl pyrrolidone, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate. In specific embodiments, an immediate release formulation included in an immediate release dosage form as disclosed herein may comprise binder levels ranging from about 1% to 10% by weight. For example, the immediate release formulation may include a binder in an amount selected from about 1%, 1.5%, 2%, 2.5%, 3%, 3.5%, 4%, 4.5%, 5%, 6%, 7%, 8%, 9%, and 10% by weight. In certain such embodiments, the amount of binder included in the immediate release formulation may range from about 1-2%, 1-3%, 1-4%, 1-5%, 1-6%, 1-7%, 1-8%, 1-9% and 1-10% by weight.

In one embodiment, the immediate release formulation comprises GHB in combination with a binder. For example, the immediate release formulation may comprise between about 90-98% by weight GHB and between about 2-10% by weight of a binder. In such an embodiment, the binder may be selected from, for example, at least one of HPMC, HPC, sodium carboxymethylcellulose, polyvinyl alcohol, povidone, and starch. In another embodiment, the immediate release formulation may include between about 90-98% by weight GHB, between about 1-5% by weight of a lubricant as described herein, and between about 1-5% by weight of a binder selected from, for example, at least one of HPMC, HPC, sodium carboxymethylcellulose, polyvinyl alcohol, povidone, and starch. In still a further embodiment, the immediate release formulation may include between about 96-98% by weight GHB, between about 1-2% by weight of a lubricant as described herein, and between about 1-2% by weight of a binder selected from, for example, at least one of HPMC, HPC, sodium carboxymethylcellulose, polyvinyl alcohol, povidone, and starch. In yet another embodiment, the immediate release formulation may include between about 96-98% by weight GHB, between about 1-2% by weight of a lubricant selected from magnesium stearate, stearic acid, sodium stearyl fumarate, and combinations thereof, and between about 1-2% by weight of a binder selected from HPMC and povidone. In particular embodiments of the immediate release formulations incorporating a binder described herein, the GHB included in such formulations may be selected from sodium oxybate and calcium oxybate.

The immediate release formulation may also include one or more surfactants. For instance, one or more surfactants may be added to formulations that may include poorly soluble excipients in order to facilitate dissolution of these excipients and, indirectly, of the drug. The addition of small amounts of surfactant to the immediate release formulations as disclosed herein may produce an increased dissolution rate. In certain embodiments, the immediate release formulation may include GHB in combination with one or more surfactants selected from, for example, ionic and non-ionic surfactants. In one such embodiment, the immediate release formulation may include at least one anionic surfactant, including docusate sodium (dioctyl sulfosuccinate sodium salt) and sodium lauryl sulfate. In yet another embodiment, the immediate release formulation may include at least one non-ionic surfactant selected from polyoxyethyelene alkyl ethers, polyoxyethylene stearates, poloxamers (e.g., polaxamer 188), polysorbate (e.g., polysorbate 80), sorbitan esters, and glyceryl monooleate. In specific embodiments, one or more surfactants included in an immediate release formulation as disclosed herein may be present, for example, in an amount of between about 0.25-2.5% by weight of the immediate release formulation. In other embodiments, one or more surfactants included in an immediate release formulation as disclosed herein may be present in an amount of up to about 3.0% by weight of the immediate release formulation. For example, in certain embodiments, the immediate release formulation may include one or more surfactants present in a range selected from about 0.01% to 3%, 0.01% to 2%, 0.01% to 1%, 0.5% to 3%, 0.5% to 2%, and 0.5% to 1% by weight of the immediate release formulation. In one such embodiment, the immediate release formulation may include about 1% by weight of a surfactant selected from polysorbate 80, poloxamer 188, sodium lauryl sulfate, and docusate sodium.

In certain embodiments, the immediate release formulations described herein include comprises GHB in combination with a surfactant and a lubricant. In one such embodiment, the immediate release formulation includes about 90-98% by weight GHB, up to about 3.0% by weight surfactant and up to about 10% by weight binder. In one such embodiment, the immediate release formulation includes about 95-98% by weight GHB, about 1-2% by weight surfactant selected from polysorbate 80, poloxamer 188, sodium lauryl sulfate, and docusate sodium, and about 1-3% by weight binder selected from HPMC and povidone. In another such embodiment, the immediate release formulation includes about 95-97.5% by weight GHB, about 0.5-1% by weight surfactant selected from polysorbate 80, poloxamer 188, sodium lauryl sulfate, and docusate sodium, about 1-2% by weight binder selected from HPMC and povidone, and about 1-2% by weight lubricant selected from magnesium stearate, stearic acid, sodium stearyl fumarate, and combinations thereof. In still another such embodiment, the immediate release formulation includes about 90-97.5% by weight GHB, about 0.5-2% by weight surfactant selected from polysorbate 80, poloxamer 188, sodium lauryl sulfate, and docusate sodium, about 1-4% by weight binder selected from HPMC and povidone, and about 1-4% by weight lubricant selected from magnesium stearate, stearic acid, sodium stearyl fumarate, and combinations thereof. In particular embodiments of the immediate release formulations incorporating a surfactant described herein, the GHB may be selected from sodium oxybate and calcium oxybate.

The immediate release formulations described herein may be manufactured using standard techniques, such as wet granulation, roller compaction, fluid bed granulation, and dry powder blending. Suitable methods for the manufacture of the immediate release formulations and unit dosage forms described herein are provided, for example, in Remington, 20$^{th}$ edition, Chapter 45 (Oral Solid Dosage Forms). It has been found that, even without the aid of binders or non-lubricating excipients, such as compression aids, wet granulation techniques can afford flowable granules with compression characteristics suitable for forming unit dosage forms as described herein. Therefore, in certain embodiments, where a drug content greater than about 85%, 90% or 95% by weight is desired for the immediate release formulation, wet granulation techniques may be used to prepare immediate release formulations as described herein. In such embodiments, as illustrated in the Examples provided herein, conventional organic or aqueous solvents may be used in the wet granulation process. Suitable wet granulation processes can be performed as fluidized bed, high shear, or low shear (wet massing) granulation techniques, as are known in the art.

In addition to one or more of a GHB drug, lubricant, binder and surfactant, where desired, the immediate release formulations described herein may also include fillers or compression aids selected from at least one of lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and sucrose. Where a filler or compression aid is used, in certain embodiments, it may be included in the immediate release formulation in an amount ranging from about 1%-15% by weight. In certain such embodiments, the immediate release formulations include about 5-10% by weight microcrystalline cellulose. In further such embodiments, the immediate release formulations include about 2.5-7.5% by weight microcrystalline cellulose.

Immediate release formulations as described herein may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of GHB over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex.

In particular, when the immediate release formulations are prepared as a tablet, the immediate release tablets contain a relatively large percentage and absolute amount of GHB and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of GHB to the subject in a relatively short period of time. For example, disintegration of a 500 mg-1.0 g tablet prepared according to the present description can provide about 80-100% of the GHB to the subject in about 30-60 minutes.

Where desired or necessary, the outer surface of an immediate release dosage form as disclosed herein may be coated with a moisture barrier layer using materials and methods known in the art. For example, where the GHB delivered by the unit dosage form is highly hygroscopic, such as, for example, where sodium oxybate is used, providing a moisture barrier layer over the immediate release dosage form as disclosed herein may be desirable. For example, protection of an immediate release dosage form as disclosed herein from water during storage may be provided or enhanced by coating the tablet with a coating of a substantially water soluble or insoluble polymer. Useful water-insoluble or water-resistant coating polymers include ethyl cellulose and polyvinyl acetates. Further water-insoluble or water resistant coating polymers include polyacrylates, polymethacrylates or the like. Suitable water-soluble polymers include polyvinyl alcohol and HPMC. Further suitable water-soluble polymers include PVP, HPC, HPEC, PEG, HEC and the like.

Methods are disclosed herein to treat conditions amenable to treatment by GHB, by administering an effective amount of one or more dosage forms as described herein. For example, the present dosage forms can be administered to treat a human afflicted with narcolepsy to reduce cataplexy and/or daytime sleepiness. Furthermore, the dosage forms disclosed herein may be useful in the treatment of a variety of conditions amenable to treatment by GHB, such as to improve the quality of sleep, or in conditions in which an increase in growth hormone levels in vivo is desired, and to treat fibromyalgia or chronic fatigue syndrome. See, U.S. Pat. No. 5,990,162. The present dosage forms may be used to treat a host of other indications including drug and alcohol abuse, anxiety, cerebrovascular diseases, central nervous system disorders, neurological disorders including Parkinson's Disease and Alzheimer Disease, Multiple Sclerosis, autism, depression, inflammatory disorders, including those of the bowel, such as irritable bowel disorder, regional illitis and ulcerative colitis, autoimmune inflammatory disorders, certain endocrine disturbances and diabetes.

The present dosage forms may also be administered for the purpose of tissue protection including protection following hypoxia/anoxia such as in stroke, organ transplantation, organ preservation, myocardial infarction or ischemia, reperfusion injury, protection following chemotherapy, radiation, progeria, or an increased level of intracranial pressure, e.g. due to head trauma. The present dosage forms can also be used to treat other pathologies believed to be caused or exacerbated by lipid peroxidation and/or free radicals, such as pathologies associated with oxidative stress, including normal aging. See, U.S. Patent Publication US 2004/009245 5 A1. The present dosage forms may also be used to treat movement disorders including restless leg syndrome, myoclonus, dystonia and/or essential tremor. See, Frucht et al, *Movement Disorders*, 20(10), 1330 (2005).

The dosage forms disclosed herein can also be provided as a kit comprising, separately packaged, a container comprising a plurality of immediate release tablets, which tablets can be individually packaged, as in foil envelopes or in a blister pack. The tablets can be packaged in many conformations with or without dessicants or other materials to preventingress of water. Instruction materials or means, such as printed labeling, can also be included for their administration, e.g., sequentially over a preselected time period and/or at preselected intervals, to yield the desired levels of sodium oxybate in vivo for preselected periods of time, to treat a preselected condition.

A daily dose of about 1-400 mg/kg of sodium oxybate or other oxybate salt such as a compound of formula (I) can be administered to accomplish the therapeutic results disclosed herein. For example, a daily dosage of about 0.5-20 g of the sodium oxybate or of a compound of formula (I) can be administered, preferably about 3-9 g, in single or divided doses. For example, useful dosages and modes of administration are disclosed in U.S. Pat. Nos. 5,990,162 and 6,472,432. Methods to extrapolate from dosages found to be effective in laboratory animals such as mice, to doses effective in humans are known to the art. See, U.S. Pat. No. 5,294,430, or 4,939, 949.

EXAMPLES

Example 1

Immediate Release Sodium Oxybate Tablets

This example compares two formulations of compressed tablets of sodium oxybate which have greater than 70% drug loading, one for which granulation was made with wet granulation and the other made by roller compaction. The composition of the tablets is summarized on Table 1, along with quantities to produce batches of 3000 tablets each.

TABLE 1

| Ingredient(s) | % (w/w) | Qty/ Unit (mg) | Batch Quantity, g |
|---|---|---|---|
| Formulation A (wet granulated) | | | |
| Sodium Oxybate | 71.4 | 750.0 | 2250.0 |
| Microcrystalline Cellulose (Avicel PH 101) | 12.1 | 126.7 | 380.1 |
| Povidone (PVP K-17) | 2.0 | 21.0 | 63.0 |
| Croscarmellose Sodium NF/EP | 12.0 | 126.0 | 378.0 |
| Colloidal Silicon Dioxide (Cab-O-Sil MP5) | 0.50 | 5.3 | 15.9 |
| Sodium Lauryl Sulfate | 1.0 | 10.5 | 31.5 |

TABLE 1-continued

| Ingredient(s) | % (w/w) | Qty/ Unit (mg) | Batch Quantity, g |
|---|---|---|---|
| Magnesium Stearate, NF (vegetable grade) | 1.0 | 10.5 | 31.5 |
| Formulation B (dry granulated) | | | |
| Sodium Oxybate | 78.9 | 750.0 | 2250.0 |
| Microcrystalline Cellulose (Avicel PH 101) | 5.9 | 55.6 | 166.8 |
| Povidone (PVP K-17) | 2.0 | 19.0 | 57.0 |
| Pregelatinized Starch (Starch 1500) | 5.0 | 47.5 | 142.5 |
| Colloidal Silicon Dioxide (Cab-O-Sil MP5) | 0.5 | 4.8 | 14.4 |
| Magnesium Stearate, NF (vegetable grade) (0.7% intragranular, 0.5% extragranular) | 1.2 | 11.4 | 34.2 |
| Croscarmellose Sodium, NF/EP (Ac-Di-Sol SD-711) (4% intragranular, 2.5% extragranular) | 6.5 | 61.8 | 185.4 |

Formulation A was produced by wet granulation in a planetary mixer. The sodium oxybate, microcrystalline cellulose, povidone, half of the sodium lauryl sulfate, and 58% of the croscarmellose sodium were pre-blended dry. The remainder of the sodium lauryl sulfate dissolved in the water used to granulate. The amount of water added was 8% of the dry powder weight. The material was mixed until uniform granules were made, then wet-sized through a #6 mesh screen, followed by oven drying at 60 C so that a final moisture content (loss on drying) was between 1.0% and 2.5%. The dried granulation was then milled through a #14 screen using a Comil. Finally, the remainder of the croscarmellose sodium was blended into the milled granulation with an 8-quart V-blender for 5 minutes, and the magnesium stearate was then added and blended for an additional 3 minutes.

To prepare Formulation B by roller compaction, first all the ingredients were hand-screened through a 20 mesh screen. All of the ingredients except the magnesium stearate and 43% of the croscarmellose sodium were transferred to an 8-quart V blender, and mixed for five minutes. The intragranular portion of the croscarmellose sodium was blended in the V-blender for 5 minutes, and finally the intragranular portion of the magnesium stearate (20.0 g) was added to the blender and mixing continued for 3 minutes. The blended powder was passed through a Vector TF-156 roller compactor set to a target pressure of 47 kg/cm$^2$, roller speed and screw speed both at 4 RPM. Ribbons with thickness of 1.4±0.05 mm were made without added water. The ribbons were granulated using an in-line rotary mill fitted with a 16-mesh screen. The granulate was added to the blender and mixed for 5 minutes. The remaining magnesium stearate (14.2 g) and croscarmellose sodium (71.4 g) was added to the blend, and mixed for 3 minutes.

Figure 1:
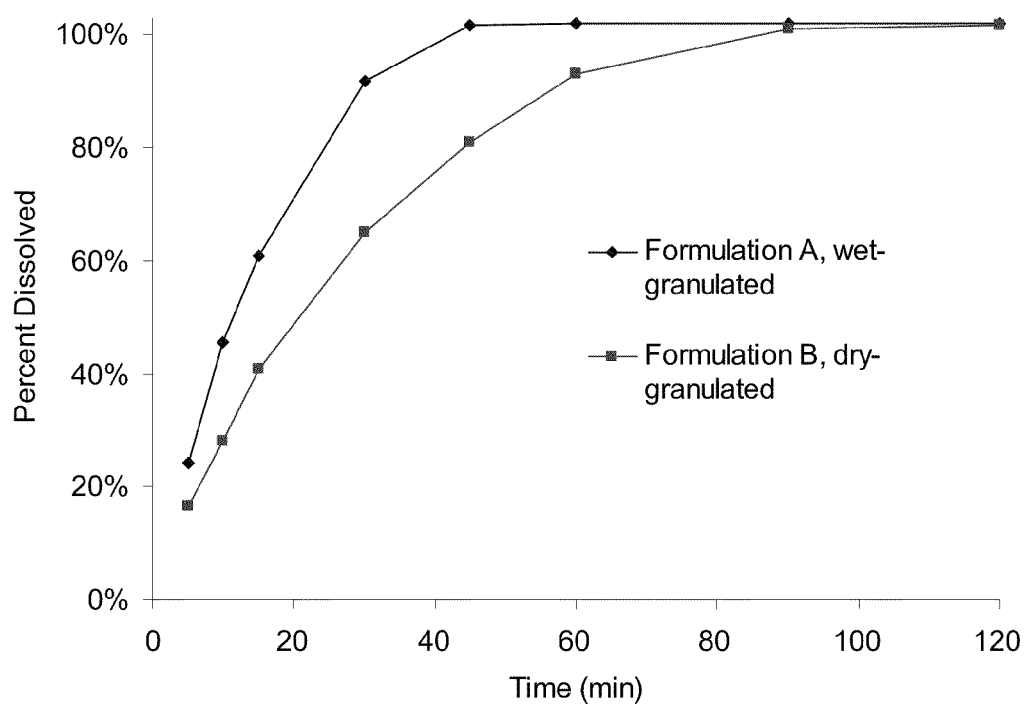
FIG. 1 is a graph depicting the dissolution profiles of wet and dry-granulated immediate release formulations as disclosed herein.

The two granulations were compressed into tablets on a 15-station standard rotary press fitted with 0.3366"×0.7283" oblong tooling. The target weights for A and B were 1050 mg and 950 mg, respectively, to achieve a target potency of 750 mg/tablet. The dissolution profiles, shown in FIG. 1, demonstrate more than 90% is dissolved in 60 minutes.

Example 2

Bioavailability and Bioequivalence of Sodium Oxybate Tablets

The formulations of Example 1 were tested for bioequivalence to sodium oxybate oral solution (Xyrem®). A Phase I, three-way, open-label, randomized single-dose crossover study of Formulation A (4.5 grams of Formulation A given as 6 tablets: Treatment A), Formulation B (4.5 grams of Formulation B given as 6 tablets: Treatment B), and Xyrem® (4.5 grams of sodium oxybate oral solution: Treatment C). Following a 1 to 21-day screening period, the study duration for each subject was approximately 7 days, Period 1 comprising Days 1 to 2, Period 2 comprising Days 3 to 4, and Period 3 Days 5 to 6. A 2-day washout period (dosing on the morning of the first day followed by a 1 day washout) separated the Treatments A, B and C.

Single doses (4.5 g, given as 6×750 mg tablets) of sodium oxybate solid dosage Formulations A and B and Single doses (4.5 g) of sodium oxybate oral solution (Xyrem®) were administered orally in the morning following a 10-hour fast, with subjects remaining fasted for a further 4 hours after dosing. The PK profile for sodium oxybate was evaluated over an 8-hour period, based on blood samples (5 mL) collected pre-dose; at 10, 20, 30, 45, 60 and 75 minutes post-dose; and at 1.5, 2, 2.5, 3, 3.5, 4, 4.5, 5, 6, 7 and 8 hours post-dose following each treatment. The PK parameters calculated for plasma sodium oxybate concentrations included: the area under the plasma concentration time curve from time 0 to time t of the last quantifiable concentration [$AUC_{0-t}$], and area under the plasma concentration time curve from time 0 to infinity [$AUC_{0-\infty}$], maximum plasma concentration of sodium oxybate ($C_{max}$), time to maximum plasma concentration ($t_{max}$), the apparent elimination rate constant ($\lambda_z$) and half-life ($t_{1/2}$) and the relative bioavailability for solid dosage Formulations A and B versus Xyrem®.

The relative bioavailability of Treatments A and B versus Treatment C (Xyrem®) based on AUC values were 98% and 100%, respectively. All treatments were found to be bioequivalent with regard to $C_{max}$ and total exposure AUC after oral administration of sodium oxybate. Since no tablet formulation can dissolve faster than Xyrem® liquid, this study suggests that any tablet formulation dissolving at least 80% in 45 minutes should be bioequivalent to Xyrem®.

TABLE 2

Summary of Mean (SD) Sodium Oxybate Pharmacokinetic Parameters

| PK Parameter | Units | | Treatment A (Test) | Treatment B (Test) | Treatment C (Reference) |
|---|---|---|---|---|---|
| $C_{max}$ | (µg/mL) | Mean | 129 | 135 | 143 |
| | | SD | 37.6 | 37.2 | 29.2 |
| | | Geometric Mean | 123 | 131 | 140 |
| | | Geometric SD | 1.39 | 1.32 | 1.23 |
| $t_{max}$ | (hr) | Median | 1.00 | 1.00 | 0.750 |
| | | Min, Max | 0.750, 2.50 | 0.500, 2.50 | 0.500, 1.50 |
| $AUC_{0-t}$ | (µg * hr/mL) | Mean | 297 | 303 | 298 |
| | | SD | 104 | 112 | 96.1 |
| | | Geometric Mean | 275 | 281 | 281 |
| | | Geometric SD | 1.53 | 1.53 | 1.45 |
| $AUC_{0-inf}$ | (µg * hr/mL) | Mean | 298 | 305 | 300 |
| | | SD | 104 | 112 | 96.4 |
| | | Geometric Mean | 277 | 282 | 283 |
| | | Geometric SD | 1.53 | 1.53 | 1.45 |
| $t_{1/2}$ | (hr) | Mean | 0.584 | 0.556 | 0.644 |
| | | SD | 0.196 | 0.128 | 0.245 |
| $\lambda_z$ | (hr$^{-1}$) | Mean | 1.29 | 1.33 | 1.19 |
| | | SD | 0.414 | 0.398 | 0.345 |

Example 3

Dry-Granulated Formulation

The roller-compaction method of granulation was chosen for further development and formulation optimization to maximize drug loading while producing tablets of acceptable quality. Two changes—addition of sodium lauryl sulfate as surfactant and removal of croscarmellose sodium—resulted in Formulation C, which has 84.2% drug loading and was successfully processed using scaled-up techniques for roller compaction described in Example 1. Table 1 shows the formulation and batch quantities to produce about 120,000 tablets.

The dry powders, except for magnesium stearate, were passed through a Fitzmill set at low speed with knives forward), then charged to a 10 cu-ft. V-blender and mixed for 130 seconds (39 revolutions). The intragranular magnesium stearate (0.534 kg) was passed through a 20-mesh screen and then added to the V-blender containing the other powders and blended for 77 seconds (23 revolutions). Roller compaction was performed on a Fitzpatrick Chilsonator (TG 99) with axially grooved rollers (1½" wide and 8" diameter) set at 8 rpm roller speed, 25 rpm horizontal screw feed, 200 rpm vertical screw speed, about 22 psi booster pressure, 750 psi roller pressure, and 6° C. chiller temperature. The material was screened through a 30" Sweeco equipped with a 14-mesh screen. About 16% of the "fines" material was passed through the chilsonator a second time. The collected product was milled through a Fitzmill, and a 100 g sample was analyzed for sieve fractions. The amount retained on 20 mesh, 40, 60, 80, 120, 200, 325-mesh, and in the pan was, respectively, 17.7.0%, 16.1%, 13.1%, 8.3%, 10.4%, 10.3%, 9.0%, and 14.1%.

To 104.2 kg of the collected granulation, 1.05 kg of magnesium stearate was added and mixed in a V-blender for 77 seconds (23 revolutions). The blended granulation was then compressed on a D-tooled Hata tablet press with 26 sets of 0.3290"×0.7120" oblong tooling. Parameters were adjusted to yield 891 mg tablet weight, 5.8-5.9 mm thickness, 9.1-13 kP hardness, and about 0.02% friability. 95.7 kg of acceptable tablets were produced.

Figure 2:
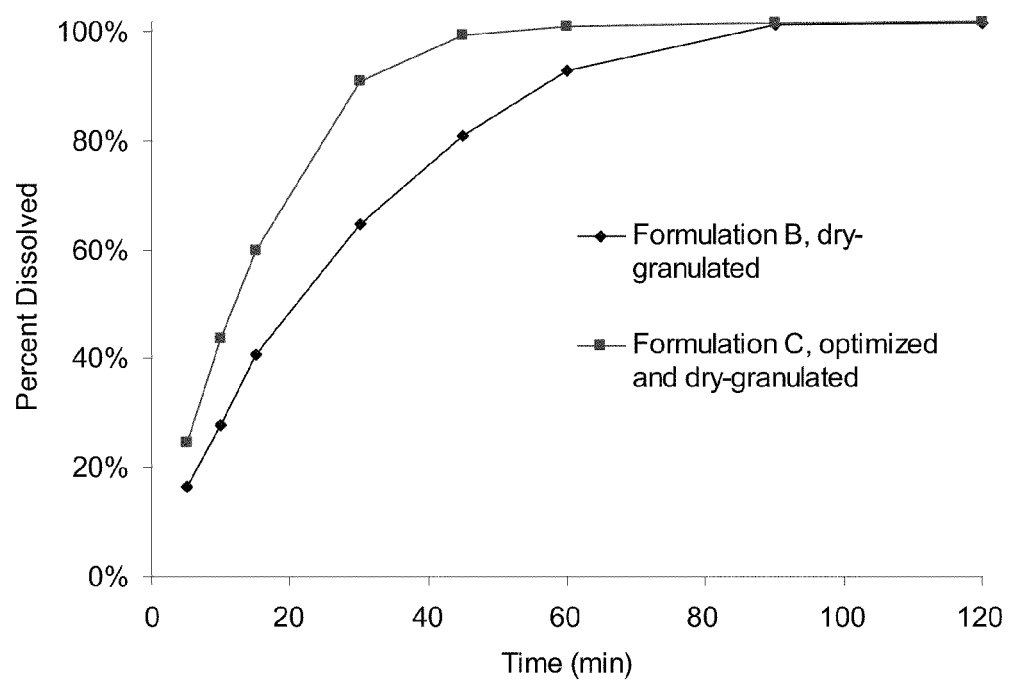
FIG. 2 is a graph showing the dissolution profiles of immediate release formulations as disclosed herein.

The dissolution profile, shown in FIG. 2, demonstrates substantially faster dissolution than that observed with the original dry-granulated product of Formulation B.

TABLE 3

Dry-Granulated Formulation C

| Ingredient(s) | % (w/w) | Qty/Unit (mg) | Batch Quantity (kg) |
|---|---|---|---|
| Sodium Oxybate | 84.17 | 750.0 | 90.00 |
| Microcrystalline Cellulose (Avicel PH 101) | 5.83 | 51.9 | 6.23 |
| Povidone (PVP K-17) | 2.00 | 17.8 | 2.14 |
| Pregelatinized Starch (Starch 1500) | 5.00 | 44.4 | 5.34 |
| Colloidal Silicon Dioxide (Cab-O-Sil MP5) | 0.50 | 4.4 | 0.53 |
| Sodium Lauryl Sulfate | 1.00 | 8.9 | 1.07 |
| Magnesium Stearate, NF (vegetable grade) (0.5% intragranular, 1.0% extragranular) | 1.50 | 13.35 | 1.60 |

Example 4

Higher Drug-Loaded Formulation for Wet Granulation

The formulation consisted of a low level of binder, a lubricant, and the sodium oxybate. The granulation was manufactured in a TK Fielder 25 L high shear granulator according to the formula in Table 1A. The binder, hydroxypropyl cellulose (Klucel EXF), was divided into two equal portions; half was dissolved in the ethanol, and half was dry blended with sodium oxybate. The material was initially granulated with 10% w/w ethanol and then titrated with another 3.5% w/w ethanol solution to achieve desired granule growth. A suitable wet mass was obtained at a total ethanol concentration of 13.5% w/w. The wet granules were divided into two sublots and then each sublot was dried in a 5-liter Niro fluid bed dryer. The dried granules were combined and milled through a Comil® equipped with a 14 mesh screen. The granulation was then blended with 2% magnesium stearate lubricant. Granulation parameters and particle size distribution are shown in Tables 4B and 4C, respectively.

TABLE 4A

Immediate-Release Tablet Formulation

| | Ingredient(s) | % w/w | mg/tablet |
|---|---|---|---|
| 1 | Sodium Oxybate | 96.0 | 750.0 |
| 2 | Hydroxypropyl cellulose, NF (Klucel EXF) | 2.0 | 15.6 |
| 3 | Ethanol, USP (200 proof)* | 13.5 | |
| 4 | Magnesium Stearate, NF | 2.0 | 15.6 |
| | TOTAL | 100.0 | 781.2 |

*Granulation solvent, removed during drying step

TABLE 4B

Granulation Parameters

Wet granulation

| | |
|---|---|
| Granulation solution addition rate (g/min) | 250 |
| Total granulation time (including solution addition and wet massing time) | 7 minutes |
| Impeller speed (rpm) | 300 |
| Chopper speed (rpm) | 1800 |

| Drying | Sublot 1 | Sublot 2 |
|---|---|---|
| Drying inlet temperature (° C.) | 70 | 70 |
| Total drying time (min) | 17 | 18 |
| Exhaust temperature at end of drying (° C.) | 47 | 48 |
| LOD (% wt loss) | 0.84 | 0.92 |

TABLE 4C

Screen Analysis of Milled Granulation

| Screen size US Std mesh | Opening size microns | Wt Retained (%) |
|---|---|---|
| 20 | 850 | 2.1 |
| 40 | 420 | 10.4 |
| 60 | 250 | 19.8 |
| 80 | 180 | 25.0 |
| 120 | 125 | 22.9 |
| 200 | 75 | 12.5 |
| Pan | <45 | 7.3 |

Example 5

Effect of Tablet Shape

The formulation of Example 4, containing 96% sodium oxybate, 2% HPC ExF, and 2% magnesium stearate, was produced in two batches using the procedures described in Example 4. One batch was compressed on a rotary press with 0.3266"×0.7283" oblong (capsule-shaped) tooling, whereas the other batch was compressed with 0.325"×0.705" modified oval tooling. In both cases, acceptable hardnesses (>10 kiloponds) and low friability were achieved. The dissolution behavior, as shown in Table 5, indicates that the oblong shape afforded substantially faster dissolution. This is likely due to a combination of a flatter surface, thinner tablet, and higher surface area.

TABLE 5

Comparison of Tablet Shape

| Tablet Shape | % Dissolved vs. Time (minutes) | | | | Minutes to dissolve: | |
|---|---|---|---|---|---|---|
| | 5 | 15 | 30 | 45 | 50% | 80% |
| 0.325" × 0.705" Oval | 24% | 42% | 58% | 68% | 22.8 | 67.2 |
| 0.3266" × 0.7283" Oblong | 26% | 47% | 65% | 78% | 17.3 | 48.6 |

Example 6

Effect of Binder Type and Solvent

Several binders were evaluated using either water or denatured alcohol as solvent. For the water-based binders, solutions or gels of 20% binder were prepared as 1.25 grams binder added to 5.0 grams water. These aqueous preparations were vigorously mixed and stored at 60° C. until used.

For the alcohol-based granulations, about 1.0 grams of binder solution (10% binder in denatured alcohol) was added to 5.0 grams sodium oxybate while stirring vigorously for about 1 minute. For the water-based granulations, about 0.5 grams of gel or solution was weighed into a beaker. A 10-fold amount of sodium oxybate was added to this, and then vigorously stirred for 1-3 minutes until granules formed. The granulations were wet sieved through a 16-mesh screen, dried at 60° C. for about 1 hour, and then dry sieved through a 16-mesh screen prior to blending required amount to obtain a 2% magnesium stearate level. For the water-based granulations, continued overnight drying (open container at 60° C.) was required.

For each granulation, four tablets of 781 mg were compressed using 0.3266"×0.7283" oblong tooling and a Carver press operated at 1-ton force and about 4-seconds dwell time. Two of the tablets were tested for hardness. The other two were tested for dissolution by USP Apparatus 2 in 900 ml of de-ionized water, with paddles rotating at 50 rpm, and two tablets dropped in each vessel. The results shown in Table 6 suggest that either water or alcohol is suitable solvent povidone and hydroxypropyl cellulose, that a variety of conventional binders are suitable for producing granulations of appropriate size and flowability, and that these granulations generally produce tablets of sufficient hardness. Furthermore, use of a binder may be optional in some circumstances.

TABLE 6

Binder Screening
Formulations contain only binder, sodium oxybate, and 2% magnesium stearate

| Binder | Solvent | Tablet Hardness (N) | % Dissolved vs. Time (minutes) | | | | Minutes to dissolve: | |
|---|---|---|---|---|---|---|---|---|
| | | | 5 | 15 | 30 | 45 | 50% | 80% |
| HPMC E5 | Water | 58 | 26% | 51% | 72% | 86% | 14.4 | 37.9 |
| HPC EF | Water | 73 | 25% | 51% | 70% | 84% | 14.7 | 40.8 |
| NaCMC 7L | Water | 73 | 24% | 49% | 68% | 82% | 15.9 | 43.1 |
| PVA | Water | 80 | 28% | 54% | 75% | 90% | 12.8 | 34.8 |
| PVP K30 | Water | 108 | 36% | 62% | 89% | 99% | 9.1 | 23.2 |
| Starch 1500 | Water | 103 | 22% | 44% | 62% | 74% | 19.2 | 55.9 |
| PVP K30 | Alcohol | 102 | 27% | 54% | 76% | 91% | 12.9 | 33.3 |
| HPC EF | Alcohol | 103 | 22% | 46% | 63% | 75% | 18.2 | 48.2 |
| No binder | Alcohol | 74 | 30% | 61% | 81% | 95% | 10.1 | 28.8 |

Binders (suppliers) in order: Hypromellose (Dow), hydroxypropyl cellulose (Ashland), sodium carboxymethyl cellulose (Ashland), polyvinyl alcohol, povidone (BASF), pregelatinized maize starch (Colorcon)

Example 7

Effect of Lubricant Level

A binder solution of 10% povidone (PVP K30) was prepared by dissolving 4.0 grams of PVP K30 (BASF) in 36.1 grams of denatured alcohol. To 19.48 grams of sodium oxybate powder, 4.00 grams of binder solution was added while mixing by hand in a beaker. The wet mass was sieved through a 16-mesh screen, dried at 60° C. for about 1 hour, and then sieved through a 16-mesh screen to yield 18.61 grams of granulation. The granulation was divided into 2.5 gram aliquots, and to each aliquot was added the required amount of magnesium stearate to make 0%, 0.5%, 1%, 1.5%, 2.0%, and 2.5% of the granulation. The lubricant was blended for approximately 30 seconds by rotating and inverting the closed container about 30 cycles.

The blends were compressed into 2 tablets each of 783 mg using 0.3266"×0.7283" oblong tooling and a Carver press operated at 1-ton force and about 4-seconds dwell time. The compressed tablets were tested for dissolution by USP Apparatus 2 in 900 ml of de-ionized water, with paddles rotating at 50 rpm, and two tablets dropped in each vessel. Assay by conductivity (dip probe) was performed at 2 minutes and then at about every 5 minutes until 50 minutes. The results are represented in Table 7 and FIG. 3.

TABLE 7

Effect of Magnesium Stearate Level

| Magnesium Stearate level | % Dissolved vs. Time (minutes) | | | | Minutes to dissolve: | |
|---|---|---|---|---|---|---|
| | 5 | 15 | 30 | 45 | 50% | 80% |
| 0.0% | 80% | 101% | 100% | 101% | 2.9 | 5.0 |
| 0.5% | 62% | 99% | 100% | 100% | 4.0 | 8.3 |
| 1.0% | 53% | 89% | 100% | 100% | 4.7 | 11.2 |
| 1.5% | 35% | 63% | 88% | 99% | 9.4 | 24.5 |
| 2.0% | 30% | 57% | 80% | 95% | 11.3 | 29.9 |
| 2.5% | 28% | 55% | 75% | 91% | 12.5 | 34.9 |

Example 8

Surfactant Screening

Several surfactants were screened for effectiveness at reducing the dissolution time of tablets. A master binder solution of 10% PVP K30 was prepared by dissolving 4.00 grams of PVP K30 in 36.1 grams of denatured alcohol. Each of the surfactants was applied in solution with the binder by adding about 0.15 grams of surfactant to 3.00 grams of the binder solution. In each case, about 4.8 grams of sodium oxybate was mixed with about 1.0 grams of surfactant-containing binder solution to form granules which were then sieved through a 16-mesh screen. After drying about 1 hour, the granulations were sieved dry through a 16-mesh screen, and compressed into two tablets each of 783 mg using 0.3266"×0.7283" oblong tooling and a Carver press operated at 1-ton force and about 4-seconds dwell time. The tablets were tested for dissolution by USP Apparatus 2 in 900 ml of de-ionized water, with paddles rotating at 50 rpm, and two tablets dropped in each vessel. Assay by conductivity (dip probe) was performed at 2 minutes and then at about every 5 minutes until 45 minutes.

The results shown are shown in Table 8.

TABLE 8

Effect of Surfactant Type
Formulations containing 2% PVP K30, 95% sodium oxybate,
2% magnesium stearate, and 1% surfactant

| Surfactant | % Dissolved vs. Time (minutes) | | | | Minutes to dissolve: | |
|---|---|---|---|---|---|---|
| | 5 | 15 | 30 | 45 | 50% | 80% |
| No surfactant* | 28% | 57% | 79% | 95% | 11.8 | 30.7 |
| Polysorbate 80 | 38% | 74% | 96% | 100% | 7.3 | 17.8 |
| Sodium lauryl sulfate | 36% | 69% | 91% | 99% | 8.5 | 20.7 |
| Poloxamer 407 | 28% | 58% | 81% | 97% | 11.5 | 29.5 |
| Poloxamer 188 | 37% | 68% | 93% | 100% | 8.3 | 21.6 |
| Docusate sodium | 37% | 75% | 97% | 100% | 7.7 | 17.4 |

*Note: "No surfactant" case is 96% SODIUM OXYBATE instead of 95% SODIUM OXYBATE

Example 9

Lubricant Type

A 15-gram batch of alcohol granulation containing 98% sodium oxybate and 2% PVP K30 was made using procedures described in Example 7. Aliquots of the granulation were then blended with three lubricants at 2% levels—magnesium stearate, stearic acid powder, and sodium stearyl fumarate (Pruv®, JRS Pharma). Four tablets of 783 mg weight (0.3266"×0.7283" oblong) were pressed, and hardness and dissolution were tested with 2 tablets. The results shown in Table 9, along with the "no lubricant" case from Example 7, indicate that sodium stearyl fumarate and stearic acid exhibit only a slight effect on dissolution.

TABLE 9

Effect of Lubricant on Hardness and
Dissolution of Sodium Oxybate Tablets
Tablets contain 96% SODIUM OXYBATE,
2% PVP K30, and 2% lubricant

| Lubricant (2% level) | Tablet Hardness (N) | % Dissolved vs. Time (minutes) | | | | Minutes dissolve: | |
|---|---|---|---|---|---|---|---|
| | | 5 | 15 | 30 | 45 | 50% | 80% |
| No lubricant* | — | 80% | 101% | 100% | 101% | 2.9 | 5.0 |
| Stearic acid | 119 | 61% | 96% | 100% | 100% | 4.1 | 9.1 |
| Sodium stearyl fumarate | 119 | 51% | 93% | 100% | 100% | 4.9 | 10.2 |
| Magnesium stearate | 102 | 27% | 54% | 76% | 91% | 12.9 | 33.3 |

*Note: "No lubricant" case from Example 7 is 98% SODIUM OXYBATE and 2% PVP K30.

Example 10

Other Tablet Strengths

The remaining granulation from Example 9 was blended with 2% sodium stearyl fumarate, and compressed into tablets of different size and shape. In all cases, 1-ton compression force and about 4-seconds dwell was used. The dissolution results shown in Table 10 confirm that tablets of 375 mg to 1500 mg strength perform comparably, with minor differences.

TABLE 10

Dissolution Performance of Other Tablet Strengths

| Strength (mg) | Mass (mg) | Tooling | Number Tested | % Dissolved vs. Time (minutes) | | | Minutes to dissolve: | |
|---|---|---|---|---|---|---|---|---|
| | | | | 5 | 15 | 30 | 50% | 80% |
| 375 | 392 | 3/8" round | 2 | 47% | 95% | 100% | 5.4 | 9.7 |
| 752 | 783 | Oblong | 2 | 51% | 93% | 100% | 4.9 | 10.2 |
| 1000 | 1042 | Oblong | 1 | 43% | 91% | 101% | 6.1 | 11.6 |
| 1500 | 1562 | Oblong | 1 | 42% | 85% | 100% | 6.4 | 13.3 |

Example 11

Calcium Oxybate Immediate Release Tablet

Calcium oxybate was prepared by generally following procedures of Example 1 found in U.S. Pat. No. 4,393,296 (Klosa, Production of Nonhygroscopic Salts of 4-Hydroxybutyric Acid). A small batch of granulation was made by first milling 8.35 grams of calcium oxybate to powder, then adding 1.66 grams of binder solution containing 10% PVP K30 in denatured alcohol. After hand mixing, granules were sized through a 16-mesh screen, and then dried for about 1 hour at 60° C. Very hard granules were made, so gentle grinding with a mortar and pestle was required in order for all dried granules to pass through a 16-mesh screen. Finally, sodium stearyl fumarate was blended in at a 2% level.

Four tablets of 783 mg weight were made using 0.3266"× 0.7283" oblong tooling and a Carver press operated at 1-ton force and about 4-seconds dwell time. Two tablets were dissolution tested. Table 11 shows a comparison of the results between sodium oxybate and calcium oxybate prepared with otherwise the same formulation and methods.

TABLE 11

Dissolution Results of Calcium Oxybate vs. Sodium Oxybate Tablets

| API | Tablet Hardness (N) | % Dissolved vs. Time (minutes) | | | Minutes to dissolve: | |
|---|---|---|---|---|---|---|
| | | 5 | 15 | 30 | 50% | 80% |
| Calcium Oxybate | 151 | 45% | 86% | 100% | 6.0 | 13.0 |
| Sodium Oxybate | 119 | 51% | 93% | 100% | 4.9 | 10.2 |

Example 12

Alcohol-Granulated Formulations

A 20-kg batch was made according to the formula in Table 12A using conditions summarized in Table 12B. The hydroxypropyl cellulose (HPC, Klucel EXF) was dissolved in 1800 g of ethanol to prepare the granulating solution. Sodium oxybate was screened through a 6 mesh Comil screen at very low RPM, and the remaining amount of HPC and sodium lauryl sulfate (SLS) were screened through a 20 mesh handscreen. The API, HPC and SLS were charged to the granulator bowl of a 150 L TK-Fielder high-shear granulator, and were dry mixed for 5 minutes. The chopper was then turned on and the granulating solution was added over 3 minutes. The materials were mixed for another 5 minutes, then dried in a fluid bed dryer to a final LOD of 0.145%.

The dry granules were milled through a comill equipped with a 14 mesh screen at 1800 rpm. Milled granules were mixed in a 2 cu ft V-blender for 5 minutes, then Pruv (previously screened through 30 mesh handscreen) was charged to the 2 cu ft V-blender and mixed for 3 minutes. The final blend was compressed at a target weight of 790 mg and hardness of 10.5 kp using a Kikusui 36 stations tablet press fitted with 0.329"×0.712" oblong B-type tooling. The dissolution results by USP 2 (37° C., 50 rpm paddles, de-ionized water) using HPLC analysis indicated 35.3% dissolved at 5 minutes, 78.5% at 15 minutes, and complete dissolution in 30 minutes.

TABLE 12A

Scaled-up Formulation using Alcohol Granulation with HPC Binder Sodium Oxybate tablet

| | Ingredients | % w/w | mg/tablet | Actual kg/batch |
|---|---|---|---|---|
| 1. | Sodium Oxybate | 95.00 | 750.00 | 19.0 |
| 2A. | Hydroxypropyl cellulose, NF (Klucel EXF) in solution | 1.00 | 7.90 | 0.20 |
| 2B. | Hydroxypropyl cellulose, NF (Klucel EXF) in the blend | 1.00 | 7.90 | 0.20 |
| 3. | Sodium Lauryl Sulfate, NF | 1.00 | 7.90 | 0.20 |
| 4. | Sodium Stearyl Fumarate, NF (Pruv) | 2.00 | 15.80 | 0.40 |
| 5. | Ethanol, USP | | | 1.80* |
| | Total | 100.0 | 789.50 | 20.00 |

*Removed during processing therefore not in the batch total.

TABLE 12B

Granulation, Drying, Milling, Compression Parameters

| Wet granulation | |
|---|---|
| Granulation solution addition rate | 600 g/min |
| Extra amount of ethanol added | none |
| Total granulation time (include solution addition and wet mass) | 3 minutes granulating solution 5 minutes wet mass |
| Impeller speed | 1800 |
| Chopper speed | 165 rpm |
| Fluid Bed Drying | |
| Inlet drying temperature | 70-74° C. |
| Exhaust temperature | 38-43° C. |
| Drying time | 10 min |
| $LOD_{final}$ | 0.145% |
| Air flow | 700-1000 cfm |
| Milling | |
| Quadro comil screen | 14 mesh |
| Impeller speed | 1800 rpm |
| Compression | |
| Compression speed | 25 rpm |

TABLE 12C

Granulation Size Distribution

| Screen size US Std mesh | Opening size microns | Unmilled granules % Retained | Milled granules % Retained |
|---|---|---|---|
| 40 | 425 | 28.2 | 5.2 |
| 60 | 250 | 20.0 | 13.7 |
| 80 | 180 | 40.9 | 53.8 |
| 120 | 125 | 7.0 | 12.8 |
| 200 | 75 | 3.7 | 11.6 |
| 325 | 45 | 0.1 | 1.9 |
| Pan | <45 | 0.0 | 1.0 |
| Total | | 100 | 100 |

Example 13

Formulation with Polyvinylpyrrolidone Binder

A formulation was demonstrated with a 20-kg batch using procedures comparable to those of Example 12. The formulation consisted of 96.25% sodium oxybate, 2.0% povidone K-30, and 1.75% sodium stearyl fumarate. The final blend was compressed at a target weight of 773 mg and hardness of 11-13 kp using a Kikusui 36 stations tablet press fitted with 0.329"×0.712" oblong B-type tooling. The dissolution results by USP 2 (37° C., 50 rpm paddles, de-ionized water) using HPLC analysis indicated 33.4% dissolved at 5 minutes, 77.7% at 15 minutes, and complete dissolution in 30 minutes.

The entire contents of all publications, patents, and patent applications referenced herein are hereby incorporated herein by reference. The compositions, dosage forms, and methods disclosed herein have been described in relation to certain preferred embodiments thereof, and many details have been set forth for purposes of illustration, it will be apparent to those skilled in the art that the invention is susceptible to additional embodiments and that certain of the details described herein may be varied without departing from the basic principles of the invention.

The invention claimed is:

1. An immediate release compressed tablet for oral delivery of GHB, the tablet comprising:
   GHB in an amount of about 90-98% by weight;
   at least one binder in an amount of about 1-5% by weight;
   at least one lubricant in an amount of about 1-5% by weight; and wherein the tablet releases at least 90% of the GHB contained therein within a period of less than one hour after administration.

2. The compressed tablet of claim 1, wherein the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate.

3. The compressed tablet of claim 1, wherein the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate.

4. The compressed tablet of claim 1, further comprising at least one surfactant, wherein the tablet comprises:
GHB in an amount of about 90-97.5% by weight;
at least one binder in an amount of about 1-4% by weight;
at least one lubricant in an amount of about 1-4% by weight; and
at least one surfactant in an amount of about 0.5-2.0% by weight.

5. The immediate release dosage form of claim 4, wherein the immediate release formulation is prepared as a solid dosage form comprising an immediate release tablet and the immediate release tablet releases at least 90% of the GHB contained therein within a period of less than one hour after administration.

6. The compressed tablet of claim 4, wherein the at least one surfactant is selected from at least one of docusate sodium (dioctyl sulfosuccinate sodium salt), sodium lauryl sulfate, a polyoxyethylene alkyl ether, a polyoxyethylene stearate, a poloxamer, a polysorbate, a sorbitan ester, and glyceryl monooleate.

7. An immediate release compressed tablet for oral delivery of a pharmaceutically acceptable salt of GHB, the tablet comprising:
about 90-98% by weight of a pharmaceutically acceptable salt of GHB selected from sodium oxybate and calcium oxybate;
at least one binder in an amount of about 1-5% by weight;
at least one lubricant in an amount of about 1-5% by weight; and
wherein the tablet releases at least 90% of the pharmaceutically acceptable salt of GHB contained therein within a period of less than one hour after administration.

8. The compressed tablet of claim 7, wherein the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate.

9. The compressed tablet of claim 7, wherein the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate.

10. The compressed tablet of claim 7, further comprising at least one surfactant, wherein the tablet comprises:
about 90-97.5% by weight of a pharmaceutically acceptable salt of GHB selected from sodium oxybate and calcium oxybate;
at least one binder in an amount of about 1-4% by weight;
at least one lubricant in an amount of about 1-4% by weight; and
at least one surfactant in an amount of about 0.5-2.0% by weight.

11. The compressed tablet of claim 10, wherein the at least one surfactant is selected from at least one of docusate sodium (dioctyl sulfosuccinate sodium salt), sodium lauryl sulfate, a polyoxyethylene alkyl ether, a polyoxyethylene stearate, a poloxamer, a polysorbate, a sorbitan ester, and glyceryl monooleate.

12. The compressed tablet of claim 7, wherein the tablet releases at least 90% of the pharmaceutically acceptable salt of GHB contained therein within a period of less than one hour after administration.

13. The immediate release dosage form of claim 10, wherein the immediate release formulation is prepared as a solid dosage form comprising an immediate release tablet and the immediate release tablet releases at least 90% of the pharmaceutically acceptable salt of GHB contained therein within a period of less than one hour after administration.

14. A method for treating an individual afflicted with cataplexy and excessive daytime sleepiness associated with narcolepsy, restless leg syndrome, essential tremor, fibromyalgia, or chronic fatigue syndrome, the method comprising:
administering an immediate release formulation for oral delivery of sodium oxybate, the immediate release formulation comprising:
sodium oxybate in an amount of about 90-98% by weight;
at least one binder in an amount of about 1-5% by weight;
at least one lubricant in an amount of about 1-5% by weight; and
wherein the immediate release dosage form releases at least 90% of the GHB contained therein within a period of less than one hour after administration.

15. The method of claim 14, wherein the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate.

16. The method of claim 14, wherein the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate.

17. The method of claim 14, wherein the immediate release formulation comprises:
GHB in an amount of about 90-97.5% by weight;
at least one binder in an amount of about 1-4% by weight;
at least one lubricant in an amount of about 1-4% by weight; and
at least one surfactant in an amount of about 0.5-2.0% by weight.

18. The method of claim 17, wherein the at least one surfactant is selected from at least one of docusate sodium (dioctyl sulfosuccinate sodium salt), sodium lauryl sulfate, a polyoxyethyelene alkyl ether, a polyoxyethylene stearate, a polaxamer, a polysorbate, a sorbitan ester, and glyceryl monooleate.

19. The method of claim 14, wherein the immediate release formulation is prepared as a solid dosage form comprising an immediate release tablet and the immediate release tablet releases at least 90% of the GHB contained therein within a period of less than one hour after administration.

* * * * *

UNITED STATES PATENT AND TRADEMARK OFFICE
CERTIFICATE OF CORRECTION

| | | |
|---|---|---|
| PATENT NO. | : 8,778,398 B2 | Page 1 of 1 |
| APPLICATION NO. | : 12/773599 | |
| DATED | : July 15, 2014 | |
| INVENTOR(S) | : Rourke et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this
Twenty-ninth Day of December, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,778,398 B2 | Page 1 of 1 |
| APPLICATION NO. | : 12/773599 | |
| DATED | : July 15, 2014 | |
| INVENTOR(S) | : Andrea Marie Rourke et al. | |

It is certified that error appears in the above-identified patent and that said Letters Patent is hereby corrected as shown below:

Title page
Item (63):
Insert --Continuation-in-Part of Application No. 12/264,709, filed on Nov. 4, 2008, now Pat. No. 8,771,735.--.

Signed and Sealed this
Sixteenth Day of August, 2016

Michelle K. Lee
*Director of the United States Patent and Trademark Office*